United States Patent
Jiang et al.

(10) Patent No.: US 10,336,931 B2
(45) Date of Patent: *Jul. 2, 2019

(54) USE OF DUAL-CATION FLUOROCARBON SURFACTANT AS AMPHIPHOBIC WETTABILITY REVERSAL AGENT IN DRILLING FLUID

(71) Applicant: CHINA UNIVERSITY OF PETROLEUM (BEIJING), Beijing (CN)

(72) Inventors: Guancheng Jiang, Beijing (CN); Deli Gao, Beijing (CN); Guangchang Ma, Beijing (CN); Jinsheng Sun, Beijing (CN); Xi Wang, Beijing (CN); Xiaolin Pu, Beijing (CN); Xianzhu Wu, Beijing (CN); Xiaoxiao Ni, Beijing (CN); Xianmin Zhang, Beijing (CN); Le Wang, Beijing (CN); Yinbo He, Beijing (CN); Fan Liu, Beijing (CN); Lili Yang, Beijing (CN); Tengfei Dong, Beijing (CN)

(73) Assignee: CHINA UNIVERSITY OF PETROLEUM (BEIJING) (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/874,438

(22) Filed: Jan. 18, 2018

(65) Prior Publication Data
US 2018/0201821 A1    Jul. 19, 2018

(30) Foreign Application Priority Data
Jan. 18, 2017   (CN) .......................... 2017 1 0038133

(51) Int. Cl.
| | |
|---|---|
| C09K 8/035 | (2006.01) |
| C09K 8/22 | (2006.01) |
| C07C 311/05 | (2006.01) |
| C07C 311/09 | (2006.01) |
| C09K 8/04 | (2006.01) |
| C09K 8/60 | (2006.01) |

(52) U.S. Cl.
CPC .............. *C09K 8/22* (2013.01); *C07C 311/05* (2013.01); *C07C 311/09* (2013.01); *C09K 8/04* (2013.01); *C09K 8/602* (2013.01)

(58) Field of Classification Search
CPC . C09K 8/035; C09K 8/12; C09K 8/68; C09K 8/52; C09K 8/887; C09K 8/467; C09K 8/80; C09K 8/62; C09K 8/42; C09K 8/64; C09K 8/36; C09K 8/72; C09K 8/74; C09K 8/82; C09K 8/516; C09K 8/70; C09K 8/512; C09K 8/032; C09K 8/38; C09K 8/60; C09K 8/22; C09K 8/24; C09K 8/40; C09K 8/44; C09K 8/50; C09K 8/76; C09K 8/32; C09K 8/54; C09K 8/06; C09K 8/28; C09K 8/34; C09K 8/46; C09K 8/487; E21B 43/16; E21B 21/003; E21B 21/062; E21B 33/13; E21B 33/14; E21B 31/03; E21B 37/00; E21B 37/06; E21B 43/12; E21B 33/138; E21B 43/006; E21B 43/04; E21B 43/25; E21B 21/01

See application file for complete search history.

(56) References Cited

U.S. PATENT DOCUMENTS

| | | | | |
|---|---|---|---|---|
| 7,164,041 B1* | 1/2007 | Moore | .................. | C07C 311/09 510/159 |
| 9,783,725 B1* | 10/2017 | Jiang | ......................... | C09K 8/12 |
| 9,783,726 B1* | 10/2017 | Jiang | ......................... | C09K 8/28 |
| 9,790,417 B1* | 10/2017 | Jiang | ......................... | C09K 8/12 |
| 9,834,717 B1* | 12/2017 | Jiang | ......................... | C09K 8/12 |

FOREIGN PATENT DOCUMENTS

CN          102389745       *  3/2012

* cited by examiner

*Primary Examiner* — Kumar R Bhushan
(74) *Attorney, Agent, or Firm* — Calfee, Halter & Griswold, LLP

(57) ABSTRACT

The present invention relates to the well drilling field in petrochemical industry, in particular to use of dual-cation fluorocarbon surfactant as amphiphobic wettability reversal agent in drilling fluid. The dual-cation fluorocarbon surfactant is a dual-cation fluorocarbon surfactant of which the cation part is represented by the following formula (1). The dual-cation fluorocarbon surfactant of the present invention can serve as wettability reversal agent when it is used for oil-gas drilling to enable rock amphiphobic, and is an amphiphobic wettability reversal agent which can cause rock surface to be non-hydrophilic and non-lipophilic. Using of dual-cation fluorocarbon surfactant, especially when drilling highly hydrous mud shale, can avoid permeation of water and oil into the rock effectively and thereby a capillary phenomenon can be prevented, and an effect of stabilizing the well wall and protecting the reservoir is attained.

Formula (1)

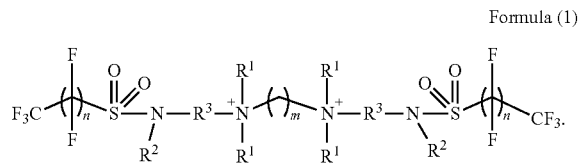

13 Claims, No Drawings

USE OF DUAL-CATION FLUOROCARBON SURFACTANT AS AMPHIPHOBIC WETTABILITY REVERSAL AGENT IN DRILLING FLUID

CROSS REFERENCE TO RELATED APPLICATIONS

This application claims priority to Chinese Application No. 201710038133.1, filed on Jan. 18, 2017, entitled "dual-cation fluorocarbon surfactant and preparation method thereof and use as amphiphobic reversal agent, drilling fluid and use thereof", which is specifically and entirely incorporated by reference.

FIELD OF THE INVENTION

The present invention relates to the well drilling field in petrochemical industry, in particular to use of dual-cation fluorocarbon surfactant as amphiphobic wettability reversal agent in drilling fluid.

BACKGROUND OF THE INVENTION

Rock wettability refers to a property that a fluid containing two immiscible phases could extend or be absorbed on a solid surface. The wettability of a rock surface such as hydrophilic or lipophilic property could reverse at a certain condition, and this reversal property is known as wettability reversal property. The change on rock wettability may directly have an effect on rock capillary pressure, oil-water relative permeability ratio, etc.

During drilling, wettability of the borehole wall rock has critical impacts on the stability of borehole wall. When rock surface is hydrophilic, free water in the drilling fluid would easily cause capillary phenomenon and permeable hydration so as to result in borehole instability. In addition, for low/ultra-low permeability reservoirs, it would be damaged very easily by invading of external fluid such damages as water blocking and water sensitivity, etc. In view of above problems, it is necessary to treat the rock surface by some methods to turn it into non-hydrophilic and non-lipophilic so as to prevent water and oil as well as capillary phenomenon, and then to maintain the stability of borehole wall and protect reservoirs.

Recently, there are mainly three types of wettability reversal surfactants for rock overseas, which are: (1) cationic surfactant, the most commonly used is cetyl trimethyl ammonium bromide (CTAB); (2) anionic surfactant, the most commonly used is polyoxyethylene (propylene) alkyl alcohol ether sulfate salt; (3) nonionic surfactant, the most commonly used is polyxyethylated alkylphenol. These surfactants do have wettability reversal function in some degree, but not sufficient to provide amphiphobicity to rock.

SUMMARY OF THE INVENTION

The present invention provides a use of dual-cation fluorocarbon surfactant as amphiphobic wettability reversal agent in drilling fluid wherein the dual-cation fluorocarbon surfactant could enable rock surface amphiphobic.

To attain the object described above, the present invention provides a dual-cation fluorocarbon surfactant, the dual-cation fluorocarbon surfactant is a dual-cation fluorocarbon surfactant of which the cation part is represented by the following formula (1):

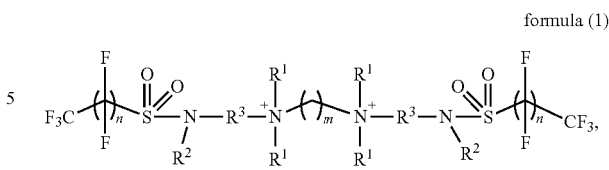

formula (1)

wherein, each $R^1$ is independently selected from C1-C6 alkyl, each $R^2$ is independently selected from H and C1-C6 alkyl, each $R^3$ is independently selected from C1-C10 alkylene, each n is independently selected from integers within a range of 3-15, and m is selected from integers within a range of 1-10.

The present invention further provides a method for preparing the dual-cation fluorocarbon surfactant, comprising: subjecting the compound represented by formula (2) and the compound represented by formula (3) to have a substitution reaction in an alcohol solvent, wherein

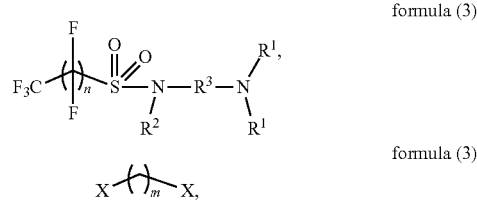

formula (3)

formula (3)

X is selected from halogen.

The present invention provides use of the dual-cation fluorocarbon surfactant as amphiphobic wettability reversal agent in drilling fluid.

The present invention provides a water-based drilling fluid containing the dual-cation fluorocarbon surfactant as amphiphobic wettability reversal agent.

The dual-cation fluorocarbon surfactant of the present invention can serve as wettability reversal agent when it is used for oil-gas drilling to enable rock amphiphobic, and is an amphiphobic wettability reversal agent which can cause rock surface to be non-hydrophilic and non-lipophilic. Using of dual-cation fluorocarbon surfactant, especially when drilling highly hydrous mud shale, can avoid permeation of water and oil into the rock effectively and thereby a capillary phenomenon can be prevented, and an effect of stabilizing the well wall and protecting the reservoir is attained.

Other features and advantages of the present invention will be further detailed in the embodiments hereunder.

DETAILED DESCRIPTION OF THE EMBODIMENTS

Hereunder some embodiments of the present invention will be detailed. It should be appreciated that the embodiments described here are only provided to describe and explain the present invention, but shall not be deemed as constituting any limitation to the present invention.

The ends points and any value in the ranges disclosed in the present invention are not limited to the exact ranges or values. Instead, those ranges or values shall be comprehended as encompassing values that are close to those ranges or values. For numeric ranges, the end points of the ranges, the end points of the ranges and the discrete point values, and the discrete point values may be combined to obtain one or more new numeric ranges, which shall be deemed as having been disclosed specifically in this document.

The present invention provides a dual-cation fluorocarbon surfactant, the dual-cation fluorocarbon surfactant is a dual-cation fluorocarbon surfactant of which the cation part is represented by the following formula (1):

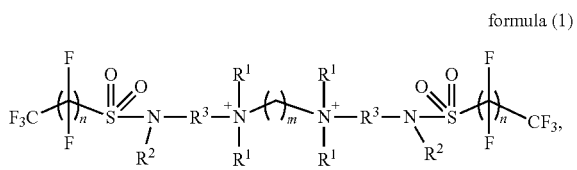

formula (1)

wherein, each $R^1$ is independently selected from C1-C6 alkyl, each $R^2$ is independently selected from H and C1-C6 alkyl, each $R^3$ is independently selected from C1-C10 alkylene, each n is independently selected from integers within a range of 3-15, and m is selected from integers within a range of 1-10.

According to the present invention, the dual-cation fluorocarbon surfactant can serve as an amphiphobic wettability reversal agent when it is used in a drilling fluid; thus, when the drilling fluid is used for oil and gas drilling, the molecules of the dual-cation fluorocarbon surfactant can be absorbed to the rock surface easily owing to the fact that the molecules have low surface tension, and thereby the rock obtains an amphiphobic property; as a result, permeation of water and oil into the rock can be avoided effectively and thereby a capillary phenomenon can be prevented, and an effect of stabilizing the well wall and protecting the reservoir is attained.

In the present invention, the C1-C6 alkyl may be methyl, ethyl, n-propyl, isopropyl, n-butyl, isobutyl, sec-butyl, tert-butyl, n-pentyl, isopentyl, n-hexyl, etc., for example.

The C1-C10 alkylene may be the alkylene formed by C1-C6 alkyl described above, or n-heptyl, n-nonyl, or n-decyl, etc.

According to the present invention, preferably, in formula (1), each R is independently selected from C1-C4 alkyl, each $R^2$ is independently selected from H and C1-C4 alkyl, each $R^3$ is independently selected from C2-C8 alkylene, each n is independently selected from integers within a range of 4-10, and m is selected from integers within a range of 2-8.

More preferably, in formula (1), each $R^1$ is independently selected from C1-C4 alkyl, each $R^2$ is independently selected from H and C1-C4 alkyl, each $R^3$ is independently selected from C2-C6 alkylene, each n is independently selected from integers within a range of 4-8, and m is selected from integers within a range of 3-6.

Further more preferably, in formula (1), each R is independently selected from methyl, ethyl, n-propyl, isopropyl, and n-butyl, each $R^2$ is independently selected from H, methyl, ethyl, n-propyl, isopropyl, and n-butyl, each $R^3$ is independently selected from —CH$_2$—CH$_2$—, —CH$_2$—CH$_2$—CH$_2$—, —CH(CH$_3$)—CH$_2$—, —CH$_2$—CH(CH$_3$)—, —CH$_2$—(CH$_2$)$_2$—CH$_2$—, —CH$_2$—(CH$_2$)—CH$_2$—, and —CH$_2$—(CH$_2$)$_4$—CH$_2$—, each n is independently selected from 4, 5, 6, 7 and 8, and m is selected from 3, 4, 5 or 6.

In a preferred embodiment of the present invention, the cation part shown in formula (1) is one of the following cations:

formula (1-1): in formula (1), each $R^1$ is methyl, each $R^2$ is H, each $R^3$ is —CH$_2$—CH$_2$—CH—, each n is 4, and m is 4;

formula (1-2): in formula (1), each $R^1$ is methyl, each $R^2$ is H, each $R^3$ is —CH$_2$—CH$_2$—CH$_2$—, each n is 6, and m is 4;

formula (1-3): in formula (1), each $R^1$ is methyl each $R^2$ is H, each $R^3$ is —CH$_2$—CH$_2$—CH$_2$—, each n is 8, and m is 4;

formula (1-4): in formula (1), each $R^1$ is methyl, each $R^2$ is H, each $R^3$ is —CH$_2$—CH$_2$—CH$_2$—, each n is 4, and m is 6.

There is no particular restriction on the anion part of the dual-cation fluorocarbon surfactant in the present invention; namely, the anion may be any conventional anion in the art, however, preferably, the anion part of the dual-cation fluorocarbon surfactant is selected from one or more of Cl$^-$, Br$^-$, and I$^-$, more preferably is Cl$^-$ or Br$^-$.

The present invention further provides a method for preparing the dual-cation fluorocarbon surfactant, comprising: subjecting the compound represented by formula (2) and the compound represented by formula (3) to have a substitution reaction in an alcohol solvent, wherein

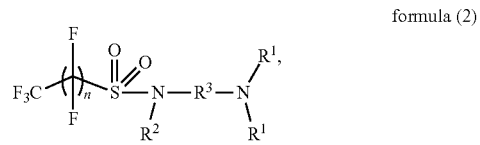

formula (2)

formula (3)

X is selected from halogen.

According to the present invention, the compound represented by formula the (2) and the compound represented by formula the (3) have a substitution reaction, so that two molecules of the compound represented by formula the (2) are linked to the two ends of a molecule of the compound represented by formula (3), forming a dual-cation fluorocarbon structure with two quaternary ammonium cations represented by formula (1).

Wherein, the compound represented by formula (2) and the compound represented by formula (3) may be selected according to the dual-cation fluorocarbon surfactant. They will not be detailed any more here.

In a preferred embodiment of the present invention, the compound represented by formula (2) is selected from one or more of compounds represented by the following formulae:

In formula (2-1): in formula (2), both $R^1$ is methyl, $R^2$ is H, $R^3$ is —CH$_2$—CH$_2$—CH$_2$—, and n is 4;
In formula (2-2): in formula (2), both $R^1$ is methyl, $R^2$ is H, $R^3$ is —CH$_2$—CH$_2$—CH$_2$—, and n is 6;
In formula (2-3): in formula (2), both $R^1$ is methyl, $R^2$ is H, $R^3$ is —CH$_2$—CH$_2$—CH$_2$—, and n is 8.

The compound represented by formula (3) is selected from one or more of compound represented by the following formulae:

In formula (3-1): in formula (3), X is Br, and m is 4;
In formula (3-2): in formula (3), X is Br, and m is 6.

According to the present invention, the compound represented by formula (2) may be a commercially available product or prepared with a conventional method in the art. For example, the method for preparing the compound represented by formula (2) may comprise: subjecting a compound represented by formula (4) and a perfluoroalkyl sulfuryl fluoride compound represented by formula (5) to have a contact reaction in the presence of a basic catalyst in an organic solvent, wherein

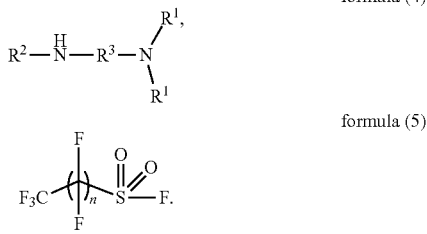

The groups involved in the formulae are those as defined above, and will not be further detailed here.

In a preferred embodiment of the present invention, the compound represented by formula (4) is selected from one or more of compounds represented by the following formulae:
In formula (4-1): in formula (4), both $R^1$ is methyl, $R^2$ is H, and $R^3$ is —$CH_2$—$CH_2$—$CH_2$— (also referred to as N,N-dimethyl-1,3-propylene diamine).

The perfluoroalkyl sulfuryl fluoride compound represented by formula (5) is selected from one or more of compounds represented by the following formulae:
In formula (5-1): in formula (5), n is 4 (also referred to as perfluorobutyl sulfuryl fluoride);
In formula (5-2): in formula (5), n is 6 (also referred to as perfluorohexyl sulfuryl fluoride);
In formula (5-3): in formula (5), n is 8 (also referred to as perfluorooctyl sulfuryl fluoride).

Wherein, the molar ratio of the compound represented by formula (4) to the perfluoroalkyl sulfuryl fluoride compound represented by formula (5) may be 1:0.8-3, for example. The basic catalyst preferably is one or more of triethylamine and/or triethanolamine. The molar ratio of the basic catalyst to the compound represented by formula (4) may be 1-3:1, for example. The organic solvent may be one or more of dichloromethane, dichloroethane, THF and DMF. With respect to 0.1 mol compound represented by formula (4), the amount of the organic solvent preferably is 150-300 mL. Preferably, the conditions of the contact reaction include: reacting at 0-10° C. for 30-100 min firstly, and then reacting at 15-40° C. for 3-6 h. To make the reaction proceed more fully, preferably, the compound represented by formula (4), the basic catalyst, and the organic solvent are mixed first, and then the perfluoroalkyl sulfuryl fluoride compound represented by formula (5) is introduced. Especially, the perfluoroalkyl sulfuryl fluoride compound represented by formula (5) is introduced by dropwise adding.

According to the present invention, in the method for preparing the dual-cation fluorocarbon surfactant, preferably, the molar ratio of the compound represented by formula (2) to the compound represented by formula (3) is 1:1-3, more preferably is 1:1-2.

According to the present invention, the alcohol solvent may be any solvent that can dissolve the compound represented by formula (2) and can be used for the substitution reaction between the compound represented by formula (2) and the compound represented by formula (3), preferably is one or more of methanol, ethanol n-propanol, isopropanol, and n-butanol. The amount of the alcohol solvent may vary within a wide range, as long as the above-mentioned substitution reaction can proceed successfully; however, to make the reaction proceed more fully and avoid wasting the solvent, preferably, with respect to 10 mmol compound represented by formula (2), the amount of the alcohol solvent is 30-100 mL (e.g., 30-60 mL).

According to the present invention, preferably, the conditions of the substitution reaction include: temperature of 60-100° C. (preferably 70-85° C.) and time of 4-10 h (preferably 5-8 h). To make the reaction proceed more fully, the alcohol solvent and the compound represented by formula (2) may be mixed first to dissolve the compound represented by formula (2) in the alcohol solvent, and then the compound represented by formula (3) may be introduced to have substitution reaction. Especially, the compound represented by formula (3) is introduced into the reaction system by dropwise adding.

According to the present invention, to extract the dual-cation fluorocarbon surfactant, the method may further comprise: cooling the product of the substitution reaction to room temperature (about 10-40° C.), and then carrying out solid-liquid separation, washing the solid phase, and drying the obtained solid, so as to obtain the dual-cation fluorocarbon surfactant.

The present invention provides use of the dual-cation fluorocarbon surfactant as amphiphobic wettability reversal agent in drilling fluid.

The present invention provides a water-based drilling fluid containing the dual-cation fluorocarbon surfactant as amphiphobic wettability reversal agent.

As described as above, according to the present invention, when the water-based drilling fluid contains the dual-cation fluorocarbon surfactant as amphiphobic wettability reversal agent, the dual-cation fluorocarbon surfactant can have an effect on the rock surface to make it amphiphobic; as a result, permeation of water and oil into the rock can be avoided effectively and thereby a capillary phenomenon can be prevented, and an effect of stabilizing the well wall and protecting the reservoir is attained.

According to the present invention, the amount of the dual-cation fluorocarbon surfactant can be selected depended upon nature of rock, preferably, based on 100 parts by weight of water in the water-based drilling fluid, amount of the dual-cation fluorocarbon surfactant is 0.1-0.5 parts by weight.

Typically, the water-based drilling fluid may contain other additives commonly used in water-based drilling fluids; preferably, the drilling fluid further contains one or more of bentonite, pH regulator, filtrate reducer, weighting agent, blocking agent, lubricant, and etc.

Wherein, the bentonite is clay with montmorillonite as the essential mineral component, and has an effect of endowing the drilling fluid with gel strength, filter loss reduction, and wall building capabilities; for example, the bentonite may be sodium bentonite and/or calcium bentonite, preferably is sodium bentonite. Based on 100 parts by weight of water in the water-based drilling fluid, preferably the content of the bentonite is 2-4 parts by weight, more preferably is 2-3 parts by weight.

Wherein, the pH regulator can ensure the drilling fluid system to be alkaline, for example, the pH regulator may be NaOH and/or KOH, preferably is NaOH. Based on 100 parts by weight of water in the water-based drilling fluid, preferably the content of the pH regulator is 0.3-0.6 parts by weight.

Wherein, the filtrate reducer can improve the filter loss reduction and wall building capabilities of the drilling fluid, for example, the filtrate reducer may be one or more of polymer filtrate reducer (e.g. Redul), PAC-LV, ammonium salt, sulfomethylated phenolic resin (e.g., SMP-I, SMP-II), sulfomethylated lignite resin (e.g., SPNH), and zwitter-ionic polymer JT-888, preferably is one or more of Redul, SMP-II and SPNH. Based on 100 parts by weight of water in the water-based drilling fluid, preferably the content of the filtrate reducer is 2-5 parts by weight.

Wherein, the anti-high temperature filtrate reducer has an effect of improving the filter loss reduction and wall building capabilities and heat resistance of the drilling fluid, for example, the anti-high temperature filtrate reducer may be one or more of anti-high temperature filtrate reducer (KLAN), KJ-1, RSTF, and etc., preferably is KJAN. Based on 100 parts by weight of water in the water-based drilling fluid, preferably the content of the anti-high temperature filtrate reducer is 1-2 parts by weight.

Wherein, the purpose of the weighting agent is to adjust the density of the drilling fluid to required density. For example, the weighting agent may be one or more of barite (e.g., barite with 90 wt. % or more barium sulfate) and organic salt (weigh-1, weigh-2 (the active ingredient is potassium formate), weigh-3, organic sodium salt GD-WT), inorganic salt (e.g. NaCl, KCl, $BaSO_4$), and etc. Based on 100 parts by weight of water in the water-based drilling fluid, preferably the content of the weighting agent is 50-100 parts by weight.

Wherein, the blocking agent has an effect of blocking the micro-pore on the borehole wall, for example, the blocking agent can be one or more of white asphalt (e.g. NFA-25), cation emulsified asphalt (YK-H), natural asphalt, sulfonated asphalt, and etc. Based on 100 parts by weight of water in the water-based drilling fluid, preferably the content of the blocking agent is 2-5 parts by weight.

Wherein, the lubricant can improve the lubricating property of the drilling fluid. For example, the lubricant may be one or more of GFR-1, FT-342, THN, and etc., preferably is GFR-1. Based on 100 parts by weight of water in the water-based drilling fluid, preferably the content of the lubricant is 0.5-2 parts by weight.

The above additives may be commercially available products, or may be prepared with conventional methods in the art. They will not be further detailed hereunder.

According to one preferred embodiment of the present invention, the water-based drilling fluid contains: 100 parts by weight of water, 0.1-0.5 parts by weight of the dual-cation fluorocarbon surfactant, 0.3-0.6 parts by weight of NaOH, 0-2 parts by weight of Redul, 1-3 parts by weight of KJAN, 2-3 parts by weight of SMP-II, 5-15 parts by weight of Weigh-2, 5-10 parts by weight of KCl, 15-30 parts by weight of NaCl, 35-50 parts by weight of $BaSO_4$, 1-3 parts by weight of NFA-25, 1-3 parts by weight of YK-H, 0.5-1.5 parts by weight of GFR-1.

The present invention further provides use of the water-based drilling fluid containing dual-cation fluorocarbon surfactant for oil-gas drilling; the dual-cation fluorocarbon surfactant is defined as above.

The dual-cation fluorocarbon surfactant of the present invention can serve as wettability reversal agent when it is used for oil-gas drilling to enable rock amphiphobic. Using of dual-cation fluorocarbon surfactant, especially when drilling highly hydrous mud shale, can avoid permeation of water and oil into the rock effectively and thereby a capillary phenomenon can be prevented, and an effect of stabilizing the well wall and protecting the reservoir is attained.

Hereunder the present invention will be detailed in embodiments.

Preparation Example 1

0.12 mol N,N'-dimethyl-1,3-propylene diamine is dissolved in 250 mL dichloromethane at 0-5° C., 0.12 mol triethylamine is added, and the mixture is mixed and stirred for 30 min; then, 0.1 mol perfluoro-butyl sulfuryl fluoride is added by dropwise adding at 0-5° C. (added completely within about 30 min, purchased from Hubei Jusheng Technology Co., Ltd. with a trade mark 375-72-4), and the mixture is held at 0-5° C. for 60 min for reaction, and then is held at 25° C. for 4 h for reaction; the obtained product is filtered, the filter cake is washed with dichloromethane, dried, and then recrystallized with acetone, thus, 128.7 g white solid is obtained. Analysis by infrared, $^1$H-NMR and $^{13}$C-NMR spectroscopy, the solid is the compound represented by formula (2-1).

Preparation Example 2

0.12 mol N,N'-dimethyl-1,3-propylene diamine is dissolved in 250 mL dichloromethane at 0-5° C., 0.12 mol triethylamine is added, and the mixture is mixed and stirred for 30 min; then, 0.1 mol perfluoro-hexyl sulfuryl fluoride is added by dropwise adding at 0-5° C. (added completely within about 30 min, purchased from Hubei xinmingtai Chemical Co., Ltd. with a trade mark 423-50-7), and the mixture is held at 0-5° C. for 60 min. For reaction, and then is held at 25° C. for 4 h for reaction; the obtained product is filtered, the filter cake is washed with dichloromethane, dried, and then recrystallized with acetone; thus, 125.3 g white solid is obtained. Analysis by infrared, $^1$H-NMR and $^{13}$C-NMR spectroscopy, the solid is the compound represented by formula (2-2).

Preparation Example 3

0.12 mol N,N'-dimethyl-1,3-propylene diamine is dissolved in 300 ml dichloromethane at 0-5° C., 0.12 mol triethylamine is added, and the mixture is mixed and stirred for 30 min; then, 0.1 mol perfluoro-octyl sulfuryl fluoride is added by dropwise adding at 0-5° C. (added completely within about 30 min, purchased from Shanghai Yijing Industrial Co., Ltd. with a trade mark 307-35-7), and the mixture is held at 0-5° C. for 60 min for reaction, and then is held at 25° C. for 4 h for reaction; the obtained product is filtered, the filter cake is washed with dichloromethane, dried, and then recrystallized with acetone; thus, 127.4 g white solid is obtained. Analysis by infrared, $^1$H-NMR and $^{13}$C-NMR spectroscopy, the solid is the compound represented by formula (2-3).

Example 1

The example is provided to describe the dual-cation fluorocarbon surfactant and preparation method thereof in the present invention.

10 mmol compound represented by formula (2-1) is dissolved in 50 mL ethanol at 65° C., and then 11 mmol 1,4-dibromobutane is added by dropwise adding (added completely within about 20 min), and the mixture is stirred for 6 h at 75° C. for reaction; the reaction product is cooled to room temperature (about 25° C.) for crystallization, and then is filtered, and the filter cake is washed and dried; thus, 12.34 g solid is obtained. Analyzed by infrared, $^1$H-NMR and $^{13}$C-NMR spectroscopy, the solid is the dual-cation fluorocarbon surfactant A1 in which the groups represented by formula (1-1) are cations and bromine ions are anions.

Example 2

The example is provided to describe the dual-cation fluorocarbon surfactant and preparation method thereof in the present invention.

10 mmol compound represented by formula (2-2) is dissolved in 50 mL ethanol at 65° C., and then 11 mmol 1,4-dibromobutane is added by dropwise adding (added completely within about 20 min), and the mixture is stirred for 6 h at 75° C. for reaction; the reaction product is cooled to room temperature (about 25° C.) for crystallization, and then is filtered, and the filter cake is washed and dried; thus, 12.43 g solid is obtained. Analyzed by infrared, $^1$H-NMR and $^{13}$C-NMR spectroscopy, the solid is the dual-cation fluorocarbon surfactant A2 in which the groups represented by formula (1-2) are cations and bromine ions are anions.

Example 3

The example is provided to describe the dual-cation fluorocarbon surfactant and preparation method thereof in the present invention.

10 mmol compound represented by formula (2-3) is dissolved in 60 mL isopropanol at 55° C., and then 12 mmol 1,4-dibromobutane is added by dropwise adding (added completely within about 20 min), and the mixture is stirred for 7 h at 85° C. for reaction; the reaction product is cooled to room temperature (about 25° C.) for crystallization, and then is filtered, and the filter cake is washed and dried; thus, 12.54 g solid is obtained. Analyzed by infrared, $^1$H-NMR and $^{13}$C-NMR spectroscopy, the solid is the dual-cation fluorocarbon surfactant A3 in which the groups represented by formula (1-3) are cations and bromine ions are anions.

Example 4

The example is provided to describe the dual-cation fluorocarbon surfactant and preparation method thereof in the present invention.

The method described in example 1 is used, but 1,6-dibromo-hexane is used in replacement of 1,4-dibromobutane; finally, 11.87 g solid is obtained. Analyzed by infrared, $^1$H-NMR and $^{13}$C-NMR spectroscopy, the solid is the dual-cation fluorocarbon surfactant A4 in which the groups represented by formula (1-4) are cations and bromine ions are anions.

Comparative Example 1

10 mmol compound represented by formula (2-3) is dissolved in 50 mL ethanol at 65° C., and then 11 mmol sodium 2-hydroxy-3-chloropropanesulfonate is added by dropwise adding (added completely within about 20 min), the pH is adjusted to 9 with sodium hydroxide solution, and the mixture is stirred for 6 h at 85° C. for reaction; the reaction product is cooled to room temperature (about 25° C.) for crystallization, and then is filtered, and the filter cake is washed and dried; thus, 10.54 g solid is obtained. Analyzed by infrared, $^1$H-NMR and $^{13}$C-NMR spectroscopy, the solid is fluorocarbon surfactant DA1 represented by formula

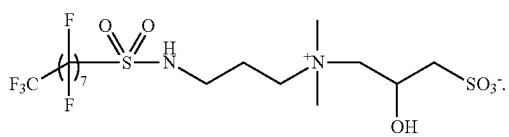

Test Case 1
1. Measurement of Amphibolic Property of Rock Surface:
1 wt. % water solution of the fluorocarbon surfactant is prepared as the fluid to be tested, 1 wt. % water solution of hexadecyl trimethyl ammonium bromide is prepared (as a comparative surfactant DA2), 1 wt. % water solution of alkyl polyoxyethylene ether sulfate (purchased from Jiangsu Haian Petrochemical Plant) is prepared (as a comparative surfactant DA3), and 1 wt. % water solution of nonyl phenol polyoxyethylene ether (purchased from Jiangsu Haian Petrochemical Plant) is prepared (as a comparative surfactant DA4), respectively, and an artificial rock core is immersed in each of the solution for 8 h at 160° C.; the rock cores are taken out, and cooled and dried naturally, and then the contact angles $\theta_o$ and $\theta_w$ of oil phase and water phase on the surfaces of rock cores are measured with a contact angle meter (JC2000D3 contact angle meter from Shanghai Zhongchen Digital Technology and Equipment Co., Ltd.). The results are shown in Table 1, wherein, the oil phase test liquid is n-hexadecane, and the water phase test liquid is distilled water.

2. Surface Tension Test:

The surface tension is measured with a TX-500C full-range spinning drop interfacial tensiometer with a spinning drop method. The main process of the spinning drop method includes: the liquid to be tested is added in an appropriate amount into a sample tube (the above-mentioned amphiphobic wettability reversal agent and the amphiphobic wettability reversal agents in the comparative examples are dissolved in distilled water to prepare solutions at different concentrations, see table 1 for the details), a bubble in appropriate size is squeezed into the sample tube, so that gas and liquid phases are formed in the sample tube; then, the sample tube is centrifuged at a high rotation speed ω=7,000 r/min, so that the low-density bubble is elongated in the high-density solution under the actions of centrifugal force, gravity, and interfacial tension. The diameter of the elongated bubble is measured, and the surface tension in the state is calculated from the diameter and the given difference in density between the two phases; in addition, the measurement temperature is 25° C. The results are shown in Table 1.

3. Influence of Wettability on Dynamic Capillary Spontaneous Imbibition

A SWT rock core spontaneous water imbibition evaluation system from Jingzhou Modern Oil Technology Development Co., Ltd. is used, liquid-wetted rock core columns and gas-wetted rock core columns are prepared from dense rock cores with similar permeability respectively (the mass fraction of the surfactant is 2 wt. % in the treatment), and a spontaneous imbibition test is carried out at room temperature (about 25° C.); in the test, air is the gas phase, and saline water and kerosene are liquid phases, wherein, the saline water is 12 wt. % NaCl solution (with 1.07 g/cm$^3$ density), the density of kerosene is 0.78 g/cm$^3$. The dynamic conditions of spontaneous oil and water imbibition of the rock cores and the final degree of liquid saturation from spontaneous imbibition are logged respectively, and the gas permeability of the rock cores after spontaneous imbibition is tested (see Table 2 for the results).

TABLE 1

| | | | Surface tension at different concentrations (mN/m) | | |
|---|---|---|---|---|---|
| Surfactant | $\theta_w/(°)$ | $\theta_o/(°)$ | 0.05 wt. % | 0.10 wt. % | 0.20 wt. % |
| Distilled water | 0 | 0 | / | / | / |
| A1 | 102.56 | 75.99 | 16.4 | 16.4 | 16.4 |
| A2 | 104.32 | 74.68 | 16.5 | 16.4 | 16.4 |

TABLE 1-continued

| Surfactant | $\theta_w/(°)$ | $\theta_o/(°)$ | Surface tension at different concentrations (mN/m) | | |
|---|---|---|---|---|---|
| | | | 0.05 wt. % | 0.10 wt. % | 0.20 wt. % |
| A3 | 103.21 | 73.86 | 16.4 | 16.5 | 16.4 |
| A4 | 105.02 | 75.45 | 16.5 | 16.4 | 16.5 |
| DA1 | 92.56 | 69.12 | 20.2 | 20.2 | 20.1 |
| DA2 | 76.23 | 48.82 | 38.1 | 38.2 | 38.1 |
| DA3 | 75.66 | 49.54 | 38.2 | 38.1 | 38.1 |
| DA4 | 77.14 | 49.08 | 38.1 | 38.1 | 38.1 |

It is seen from the results in Table 1: the dual-cation fluorocarbon surfactant provided in the present invention makes the rock surface amphiphobic, wherein, the water wetting angle is up to 1000 or above, and the n-hexadecane wetting angle is up to 700 or above; in addition, the surface tension is decreased.

TABLE 2

| Agent | $V_p$ | $m_0$ | Liquid | m(single) | s(single) | m(reverse) | s(reverse) |
|---|---|---|---|---|---|---|---|
| Blank | 1.875 | 69.38 | Saline water | 70.55 | 62.47 | 70.90 | 81.12 |
| | 1.757 | 68.69 | Kerosene | 69.53 | 59.75 | 69.81 | 79.43 |
| A1 | 1.744 | 68.53 | Saline water | 68.79 | 18.84 | 68.90 | 26.34 |
| | 1.704 | 68.07 | Kerosene | 68.31 | 17.24 | 68.51 | 32.16 |
| A2 | 1.742 | 68.51 | Saline water | 68.83 | 18.62 | 68.87 | 26.03 |
| | 1.704 | 68.05 | Kerosene | 68.28 | 17.12 | 68.49 | 31.95 |
| A3 | 1.748 | 68.51 | Saline water | 68.77 | 18.89 | 68.88 | 26.41 |
| | 1.706 | 68.05 | Kerosene | 68.29 | 17.28 | 68.49 | 32.22 |
| A4 | 1.738 | 68.42 | Saline water | 68.68 | 18.76 | 68.78 | 26.25 |
| | 1.702 | 68.02 | Kerosene | 68.25 | 17.18 | 68.46 | 32.13 |
| DA1 | 1.756 | 68.52 | Saline water | 68.80 | 19.79 | 69.03 | 36.45 |
| | 1.712 | 68.12 | Kerosene | 68.37 | 18.16 | 68.71 | 42.83 |
| DA2 | 1.795 | 68.84 | Saline water | 69.22 | 26.44 | 69.39 | 38.21 |
| | 1.722 | 68.47 | Kerosene | 68.81 | 24.95 | 69.07 | 43.48 |
| DA3 | 1.798 | 68.84 | Saline water | 69.22 | 26.43 | 69.38 | 37.46 |
| | 1.722 | 68.46 | Kerosene | 68.80 | 24.93 | 69.05 | 43.04 |
| DA4 | 1.798 | 68.84 | Saline water | 69.22 | 26.45 | 69.38 | 37.47 |
| | 1.724 | 68.46 | Kerosene | 68.80 | 24.94 | 69.05 | 43.03 |

Note:
"blank" represents no amphiphobic agent; "$V_p$" represents volume of permeation; "$m_0$" represents mass of permeation; "m(single)" represents rock core mass after spontaneous imbibition in single direction; "s(single)" represents degree of liquid saturation in the rock core after spontaneous imbibition in single direction; "m(reverse)" represents rock core mass after spontaneous imbibition in reverse direction; "s(reverse)" represents degree of liquid saturation in the rock core after spontaneous imbibition in reverse direction.

It is seen from Table 2: after the dual-cation fluorocarbon surfactant obtained in the present invention is added as an amphiphobic wettability reversal agent, all of the "$V_p$", "$M_0$", "m(single)", "s(single)", "m(reverse)", and "s(reverse)" are decreased, indicating that the dual-cation fluorocarbon surfactant obtained in the present invention has a favorable amphiphobic effect.

Drilling Fluid Example 1

The example is provided to describe the drilling fluid of the present invention.

The formulation is: 100 parts by weight of water, 0.1 parts by weight of dual-cation fluorocarbon surfactant A1, 3 parts by weight of sodium bentonite (purchased from Weifang Huawei Research Center of Bentonite Technology, as the same below), 0.5 parts by weight of NaOH, 1.5 parts by weight of filtrate reducer purchased from (purchased from CNPC Bohai Drilling Engineering Co., Ltd. with trade mark Redul, as the same below), 1.5 parts by weight of anti-high temperature filtrate reducer (purchased from Shijiazhuang Hualai Dingsheng Technology Co., Ltd. with trade mark KJAN, as the same below), 10 parts by weight of Weigh-2 (purchased from Tianjing CNPC Boxing Engineering Technology Co., Ltd. with trade mark Weigh-2, as the same below), 8 parts by weight of KCl, 2 parts by weight of white asphalt (purchased from Shijiazhuang Hualai Dingsheng Technology Co., Ltd. with trade mark NFA-25, as the same below), 2 parts by weight of blocking agent (purchased from Puyang Green Industry Polymer Co., Ltd with trade mark YK-H, as the same below), 1 part by weight of lubricant (purchased from Shijiazhuang Hualai Dingsheng Technology Co., Ltd. with trade mark GFR-1, as the same below), 42 parts by weight of $BaSO_4$, 25 parts by weight of NaCl; thus, a drilling fluid Y1 is prepared.

Drilling Fluid Example 2-4 and Drilling Fluid Comparative Example 1

According to the formation of the drilling fluid example 1, wherein the difference is using the dual-cation fluorocarbon surfactant A2-A4 and DA1, and above-mentioned surfactant DA2-DA4 to replace the dual-cation fluorocarbon surfactant A1 respectively, thus, drilling fluid Y2-Y4 and DY1-DY4 are prepared respectively.

Test Case 2

Testing basic properties of the drilling fluids: the drilling fluids Y1-Y4 and DY1-DY4 are tested at room temperature without hot aging and after hot aging at 150° C. for 16 h respectively, to test their gel strength (GEL, i.e., initial gel strength ($G_{10}$)/final gel strength ($G_{10'}$)), apparent viscosity (AV), plastic viscosity (PV), yield point (YP), ratio of yield point to plastic viscosity (YP/PV), high-temperature and high-pressure filtration (HTHL), API filtration (API), density, and pH. The results are shown in Table 3, wherein:

The GEL strength refers to the strength of the gel structure formed after the drilling fluid enters into a still state, i.e., the ratio of initial gel strength to final gel strength, in unit of Pa/Pa; wherein, the initial gel strength and final gel strength are measured with a FANN six-speed viscosity meter with the method specified in the national standard GB/T29170-2012:

Initial_Gel_Strength = $0.5\theta_3$(10 s)

Final_Gel_Strength = $0.5\theta_3$(10 min).

The apparent viscosity (AV) is measured with a FANN six-speed viscosity meter with the method specified in the national standard GB/T29170-2012, in unit of mpa·s, AV=½$\theta_{600}$.

The plastic viscosity (PV) is measured with a FANN six-speed viscosity meter with the method specified in the national standard GB/T29170-2012, in unit of mPa·s, PV=$\theta_{600}$-$\theta_{300}$.

The yield point (YP) is measured with a FANN six-speed viscosity meter with the method specified in the national standard GB/29170-2012, YP=0.5(2$\theta_{300}$-$\theta_{600}$), in unit of Pa.

The ratio of yield point to plastic viscosity is $$\frac{YP}{\varphi 600 - \varphi 300},$$

where, $\varphi$600 and $\varphi$300 are read with a six-speed viscosity meter in sequence.

HTHP refers to high-temperature and high-pressure filter loss, and is measured with a HTHP filter loss meter with the method specified in the national standard GB/T29170-2012, in unit of mL.

API refers to intermediate pressure filter loss, and is measured with an API filter loss meter with the method specified in the standard SY/T5621-93, in unit of mL.

DY4 respectively to measure the contact angles $\theta_o$ and $\theta_w$ of oil phase and water phase on the surfaces of rock cores, the results are shown in Table 4.

TABLE 4

| Drilling fluid | $\theta_w$/(°) | $\theta_o$/(°) |
|---|---|---|
| Blank | 30.8 | 32.4 |
| Y1 | 105.4 | 92.5 |
| Y2 | 106.6 | 98.2 |
| Y3 | 103.9 | 94.7 |
| Y4 | 100.6 | 93.3 |
| DY1 | 96.2 | 86.9 |
| DY2 | 74.6 | 61.3 |
| DY3 | 77.9 | 60.8 |
| DY4 | 75.6 | 59.5 |

Note:
Blank means a drilling fluid Y1 without A1.

It is seen from Table 4, by adding the dual-cation fluorocarbon surfactant of the present invention as amphiphobic wettability reversal agent, the contact angle of rock core wetted by the drilling fluid greatly increases, and the rock core wetted by the drilling fluid would exhibits supper amphiphobic property.

While some preferred embodiments of the present invention are described above, the present invention is not limited to the details in those embodiments. Those skilled in the art can make modifications and variations to the technical scheme of the present invention, without departing from the spirit of the present invention. However, all these modifications and variations shall be deemed as falling into the protected scope of the present invention.

TABLE 3

| Drilling Fluid | G10" | G10' | AV mPa·s | PV mPa·s | YP Pa | YP/PV | HTHP mL | API mL | Density g/cm³ | pH |
|---|---|---|---|---|---|---|---|---|---|---|
| Before hot aging | | | | | | | | | | |
| Blank | 1.5 | 4 | 56 | 46 | 10 | 0.217 | / | 2 | 1.45 | 8.5 |
| Y1 | 1.5 | 4 | 56 | 46 | 10 | 0.217 | / | 1.8 | 1.45 | 8.5 |
| Y2 | 1.5 | 4 | 56 | 45 | 11 | 0.244 | / | 7 | 1.45 | 8.5 |
| Y3 | 1.5 | 4 | 57 | 46 | 11 | 0.239 | / | 2 | 1.45 | 8.5 |
| Y4 | 1 | 4 | 54.5 | 45 | 9.5 | 0.211 | / | 2.2 | 1.45 | 8.5 |
| DY1 | 1.5 | 4 | 56.5 | 46 | 10.5 | 0.228 | / | 1.8 | 1.45 | 8.5 |
| DY2 | 1.5 | 4 | 55 | 45 | 10 | 0.222 | / | 2 | 1.45 | 8.5 |
| DY3 | 1.5 | 4 | 56 | 46 | 10 | 0.217 | / | 2 | 1.45 | 8.5 |
| DY4 | 1 | 3.5 | 54.5 | 45 | 9.5 | 0.211 | / | 2.2 | 1.45 | 8.5 |
| After hot aging at 150° C. for 16 h | | | | | | | | | | |
| Blank | 0.5 | 2 | 44 | 36 | 8 | 0.222 | 8.4 | 2.6 | 1.46 | 8.5 |
| Y1 | 0.5 | 1.5 | 43.5 | 36 | 7.5 | 0.208 | 8.6 | 2.8 | 1.46 | 8.5 |
| Y2 | 0.5 | 2 | 44 | 36 | 8 | 0.222 | 8.2 | 2.4 | 1.46 | 8.5 |
| Y3 | 0.5 | 1.5 | 42 | 35 | 7 | 0.200 | 8.8 | 2.8 | 1.46 | 8.5 |
| Y4 | 0.5 | 2 | 45.5 | 37 | 8.5 | 0.230 | 8.4 | 2.6 | 1.46 | 8.5 |
| DY1 | 0.5 | 1.5 | 43.5 | 36 | 7.5 | 0.208 | 8.2 | 2.2 | 1.46 | 8.5 |
| DY2 | 0.5 | 2 | 45 | 37 | 8 | 0.216 | 8.4 | 2.6 | 1.46 | 8.5 |
| DY3 | 0.5 | 2 | 44 | 36 | 8 | 0.222 | 8.4 | 2.6 | 1.46 | 8.5 |
| DY4 | 0.5 | 1.5 | 42.5 | 35 | 7.5 | 0.214 | 8.8 | 2.8 | 1.46 | 8.5 |

Note:
Blank means a drilling fluid Y1 without A1.

It is seen from Table 3, the dual-cation fluorocarbon surfactant of the present invention has low impact on rheological property and filter loss properties of the drilling fluid system.

Test Case 3

According to the test profile of the test case 1, artificial rock cores are put into the drilling fluid Y1-Y4 and DY1-

In addition, it should be noted that the specific technical features described in above embodiments can be combined in any appropriate form, provided that there is no conflict. To avoid unnecessary repetition, the possible combinations are not described specifically in the present invention.

Moreover, different embodiments of the present invention can be combined freely as required, as long as the combinations don't deviate from the ideal and spirit of the present invention. However, such combinations shall also be deemed as falling into the scope disclosed in the present invention.

The invention claimed is:

1. A wettability reversal agent for use in a drilling fluid, the wettability reversal agent comprising a dual-cation fluorocarbon surfactant, of which the cation part is represented by formula (1):

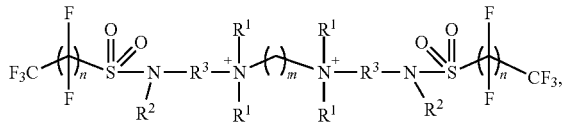

formula (1)

wherein, each $R^1$ is independently selected from C1-C6 alkyl, each $R^2$ is independently selected from H and C1-C6 alkyl, each $R^3$ is independently selected from C1-C10 alkylene, each n is independently 5-15, and m is 1-10.

2. The wettability reversal agent according to claim 1, wherein each $R^1$ is independently selected from C1-C4 alkyl, each $R^2$ is independently selected from H and C1-C4 alkyl, each $R^3$ is independently selected from C2-C8 alkylene, each n is independently selected from 5-10, and m is 2-8.

3. The wettability reversal agent according to claim 2, wherein each $R^3$ is independently selected from C2-C6 alkylene, each n is independently selected from 5-8, and m is 3-6.

4. The wettability reversal agent according to claim 3, wherein each $R^1$ is independently selected from methyl, ethyl, n-propyl, isopropyl, and n-butyl, each $R^2$ is independently selected from H, methyl, ethyl, n-propyl, isopropyl, and n-butyl, each $R^3$ is independently selected from —CH$_2$—CH$_2$—, —CH$_2$—CH$_2$—CH$_2$—, —CH(CH$_3$)—CH$_2$—, —CH$_2$—CH(CH$_3$)—, —CH$_2$—(CH$_2$)$_2$—CH$_2$—, —CH$_2$—(CH$_2$)$_3$—CH$_2$—, and —CH$_2$—(CH$_2$)$_4$—CH$_2$—, each n is independently selected from 5, 6, 7 and 8, and m is selected from 3, 4, 5 and 6.

5. The wettability reversal agent according to claim 1, wherein the cation part shown in formula (1) is one of the following cations:

formula (1-2): in formula (1), each $R^1$ is methyl, each $R^2$ is H, each $R^3$ is —CH$_2$—CH$_2$—CH$_2$—, each n is 6, and m is 4; and formula (1-3): in formula (1), each $R^1$ is methyl, each $R^2$ is H, each $R^3$ is —CH$_2$—CH$_2$—CH$_2$—, each n is 8, and m is 4.

6. The wettability reversal agent according to claim 1, wherein anion part of the dual-cation fluorocarbon surfactant is selected from Cl$^-$, Br$^-$, I$^-$, and combinations thereof.

7. A water-based drilling fluid containing a dual-cation fluorocarbon surfactant for oil-gas drilling; the dual-cation fluorocarbon surfactant comprising a cation part which is represented by formula (1):

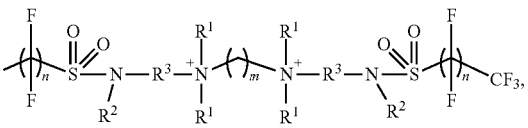

formula (1)

wherein, each $R^1$ is independently selected from C1-C6 alkyl, each $R^2$ is independently selected from H and C1-C6 alkyl, each $R^3$ is independently selected from C1-C10 alkylene, each n is independently 5-15, and m is 1-10.

8. The water-based drilling fluid according to claim 7, wherein based on 100 parts by weight of water in the water-based drilling fluid, amount of the dual-cation fluorocarbon surfactant is 0.1-0.5 parts by weight.

9. The water-based drilling fluid according to claim 7, wherein each $R^1$ is independently selected from C1-C4 alkyl, each $R^2$ is independently selected from H and C1-C4 alkyl, each $R^3$ is independently selected from C2-C8 alkylene, each n is independently selected from 5-10, and m is 2-8.

10. The water-based drilling fluid according to claim 9, wherein each $R^3$ is independently selected from C2-C6 alkylene, each n is independently selected from 5-8, and m is 3-6.

11. The water-based drilling fluid according to claim 10, wherein in formula (1), each $R^1$ is independently selected from methyl, ethyl, n-propyl, isopropyl, and n-butyl, each $R^2$ is independently selected from H, methyl, ethyl, n-propyl, isopropyl, and n-butyl, each $R^3$ is independently selected from —CH$_2$—CH$_2$—, —CH$_2$—CH$_2$—CH$_2$—, —CH(CH$_3$)—CH$_2$—, —CH$_2$—CH(CH$_3$)—, —CH$_2$—(CH$_2$)$_2$—CH$_2$—, —CH$_2$—(CH$_2$)$_3$—CH$_2$—, and —CH$_2$—(CH$_2$)$_4$—CH$_2$—, each n is independently selected from 5, 6, 7 and 8, and m is selected from 3, 4, 5 and 6.

12. The water-based drilling fluid according to claim 7, wherein the cation part shown in formula (1) is one of the following cations:

formula (1-2): in formula (1), each $R^1$ is methyl, each $R^2$ is H, each $R^3$ is —CH$_2$—CH$_2$—CH$_2$—, each n is 6, and m is 4; and formula (1-3): in formula (1), each $R^1$ is methyl, each $R^2$ is H, each $R^3$ is —CH$_2$—CH$_2$—CH$_2$—, each n is 8, and m is 4.

13. The water-based drilling fluid according to claim 7, wherein anion part of the dual-cation fluorocarbon surfactant is selected from Cl$^-$, Br$^-$, I$^-$, and combinations thereof.

* * * * *